(12) United States Patent
Randhava et al.

(10) Patent No.: US 9,382,558 B2
(45) Date of Patent: Jul. 5, 2016

(54) FATTY ACIDS FROM PHYTOPLANKTON

(75) Inventors: Surjit Singh Randhava, Evanston, IL (US); Sarabjit Singh Randhava, Evanston, IL (US); Richard Kao, Northbrook, IL (US); Todd Harvey, Schaumburg, IL (US); Ajaib Singh Randhava, Streamwood, IL (US); Gregory Dicosola, Westmont, IL (US)

(73) Assignee: UNITEL TECHNOLOGIES, INC., Mt. Prospect, IL (US)

( * ) Notice: Subject to any disclaimer, the term of this patent is extended or adjusted under 35 U.S.C. 154(b) by 159 days.

(21) Appl. No.: 13/191,660

(22) Filed: Jul. 27, 2011

(65) Prior Publication Data
US 2013/0287917 A1    Oct. 31, 2013

(51) Int. Cl.
C11B 1/00      (2006.01)
C12P 7/64      (2006.01)
A23K 1/00      (2006.01)
C11B 1/02      (2006.01)
C11C 1/04      (2006.01)

(52) U.S. Cl.
CPC ............... *C12P 7/6409* (2013.01); *A23K 1/008* (2013.01); *C11B 1/02* (2013.01); *C11C 1/04* (2013.01); *Y02E 50/13* (2013.01)

(58) Field of Classification Search
CPC .................................... C11B 1/02; C11C 1/04
USPC ....................................................... 554/2, 23
See application file for complete search history.

*Primary Examiner* — Deborah D Carr

(57) ABSTRACT

This invention relates to a new process for making fatty acids directly from a feedstock consisting of phytoplankton in water without the need to a) thermally separate, dewater and dry the phytoplankton, and b) extract the immobilized lipids. Our method is much less expensive than the current practice of making fatty acids from phytoplankton, because we bypass the costly and energy intensive operations associated with a) dewatering and drying the biomass, and b) extracting the immobilized lipids. As such, this invention greatly enhances the economic viability of making biofuels and bioproducts from phytoplankton.

18 Claims, 6 Drawing Sheets

FATTY ACIDS FROM PHYTOPLANKTON

BACKGROUND DISCUSSION

Worldwide interest in converting phytoplankton into biofuels and bioproducts has grown to an unprecedented level over the last decade. An untold number of companies and organizations are now actively engaged in developing and commercializing a variety of pathways to make sensible use of this highly renewable and seemingly limitless resource. During 2009 and 2010, the US Department of Energy has provided a significant amount of financial support for programs in this field, and that in turn has spurred the inflow of hundreds of millions of dollars in venture and investment banking capital.

Most of the excitement about phytoplankton has to do with its exceptionally high and bountiful per unit area yield of lipids—5,000 to 20,000 US gallons per acre per year—7 to 30 times greater than the next best agricultural crop. More than 300,000 types of phytoplankton have been identified, and the lipid content can range from 5 wt % to 60 wt % by weight. In addition to the lipids, phytoplankton also contain carbohydrates and protein, compounds that can also be converted into additional biofuels and bioproducts, and/or food for human and animal consumption. FIG. 1 illustrates the distribution of lipids, carbohydrates and protein in a typical class of phytoplankton.

Phytoplankton in general have the approximate formula $C_{108}H_{180}O_{45}N_{16}S$. Because their carbon is derived from $CO_2$, their nitrogen from $NH_4^+$, most of their hydrogen from water, and most of their oxygen they evolve comes from $CO_2$. We may write the following stoichiometric formula for the using of phytoplankton to provide photosynthetic carbon fixation:

$$106CO_2 + 236H_2O + 16NH^+_4 + SO_4^= \longrightarrow$$
Wt: 4665.05
$$C_{106}H_{180}O_{45}N_{16}S + 118O_2 + 171 H_2O + 14H^+$$
$$2430.75 \quad\quad 3775.86$$

| Components | Molar Ratio | Wt. Ratio |
|---|---|---|
| $O_2$/Phytoplankton | 118 | 1.5534 |
| $CO_2$/Phytoplankton | 106 | 1.9192 |
| $O_2/CO_2$ | 1.1132 | 0.8094 |

TABLE 1

CHEMICAL COMPOSITION (WT % DRY BASIS) OF PHYTOPLANKTON

| | Wt % (Dry) |
|---|---|
| Components | |
| Carbohydrates | 40 |
| Protein | 30 |
| Lipids | 30 |
| Total | 100 |
| Chemical Analysis | |
| C | 52.3782 |
| H | 7.4636 |
| O | 29.6194 |
| N | 9.2197 |
| S | 1.3191 |
| TOTAL | 100.0000 |

The net effort is that when one mole of phytoplankton is produced, 106 moles of $CO_2$ are removed from the air and meanwhile 118 moles of $O_2$ are released to the atmosphere in the presence of an excess of water.

The above photosynthetic carbon fixation process has tremendous value when applied to industrial sources of $CO_2$ emissions such as fossil fuel fired power generation, cement manufacturing, etc.

The above situation notwithstanding, almost every phytoplankton-based technology and process that is presently being developed has one thing in common, and that has to do with the need to extract the immobilized lipids at some intermediate stage. The universal focus of attention in this emerging industry has to do with the term "extraction," as in the extraction of lipids.

Unfortunately, it has become increasingly apparent that the extraction of immobilized lipids from phytoplankton at a commercial scale is very expensive, both in terms of capital and operating costs, especially with respect to energy consumption. In a laboratory environment, when dealing with a few hundred pounds of phytoplankton feedstock, most lipid extraction methods look promising, albeit some more than others. However, simple extrapolation of these results without careful consideration to energy consumption can often be highly misleading. We have actually analyzed proposed processes in which the energy used to extract the lipids is greater than the energy value of the end product.

Significance of Our Invention

Our invention is unique insofar that the process is intended to "react" rather than "extract" the immobilized lipids. In a practical sense, we bypass the extraction step and directly convert the immobilized lipids contained in the phytoplankton slurry into fatty acids. We need almost no dewatering and absolutely no drying of the phytoplankton, thereby affecting significant savings in capital equipment and energy costs. Subsequently, since we do not extract the lipids, we save even more in terms of capital and energy.

End Product Applications

The fatty acids manufactured by our process can be used as a feedstock for making the following biofuels and bioproducts:

Biodiesel (methyl ester) by catalytic distillation of the fatty acids with methanol.

Biodiesel (ethyl ester) by catalytic distillation of the fatty acids with ethanol - suitable in countries such as Brazil with low cost ethanol supplies.

Biolubricants (higher alkyl esters) by catalytic distillation of the fatty acids with higher alcohols such as octanol.

Green diesel by catalytic hydroprocessing of the fatty acids.

Biojet fuels by 1) catalytic decarboxylation of the fatty acids to make paraffinic hydrocarbons, followed by 2) mild hydrocracking and hydroisomerization of the paraffinic hydrocarbons to $C_{10}$-$C_{15}$ branched paraffins (jet fuel).

Fatty alcohols by catalytic hydrogenation of the fatty acids.

Valuable Byproduct

After the immobilized lipids have been reacted to make fatty acids, and this fatty acid product has been separated, the deoiled phytoplankton biomass that remains is dried and processed for use as a high protein food for human or animal consumption.

BRIEF DESCRIPTION OF THE DRAWINGS

These and other objects and features of this invention will be better understood from the following detailed description taken in conjunction with the drawings wherein.

PROCESS DESCRIPTION

Figure 1:
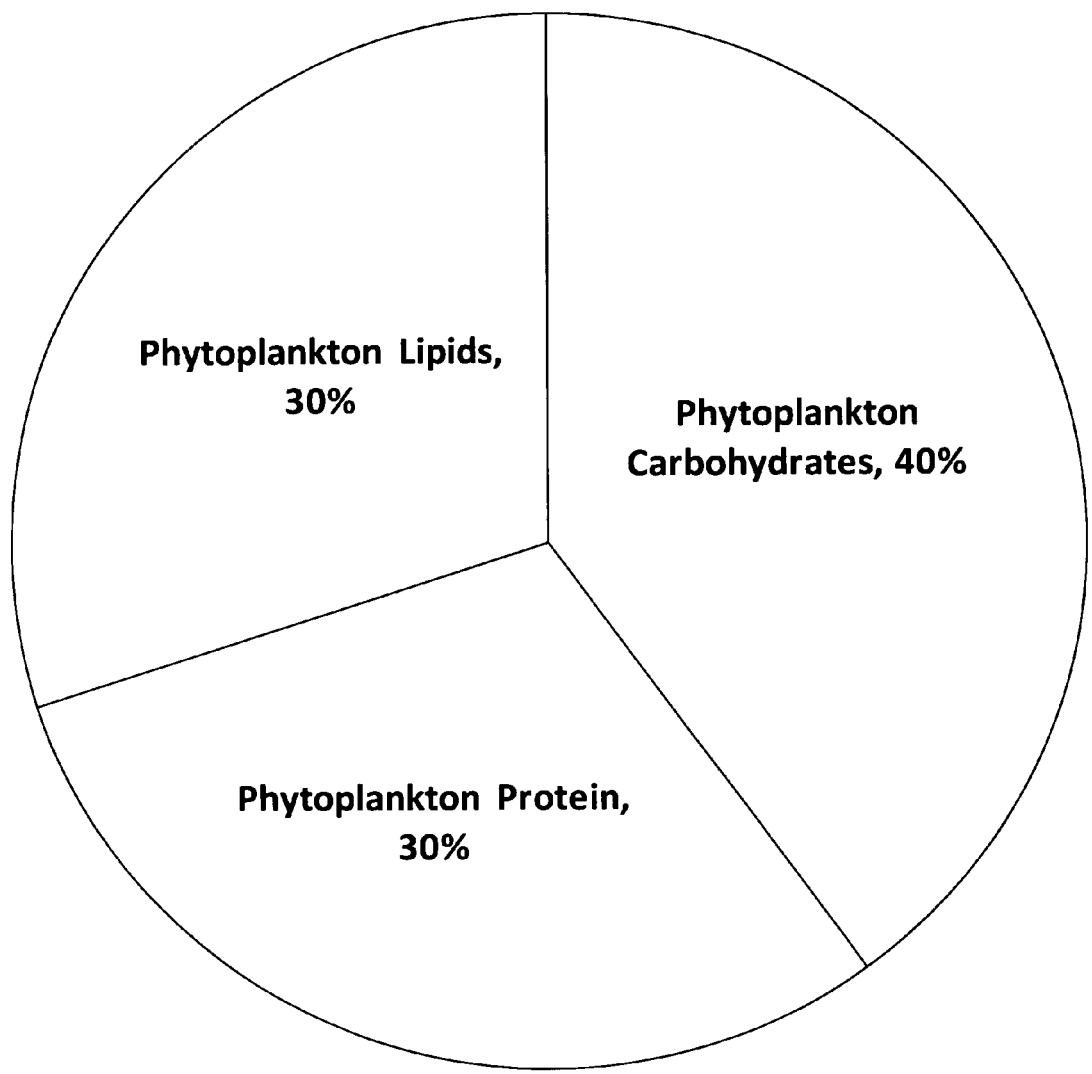
FIG. 1 is a pie chart showing the composition of a typical phytoplankton.
Figure 2:
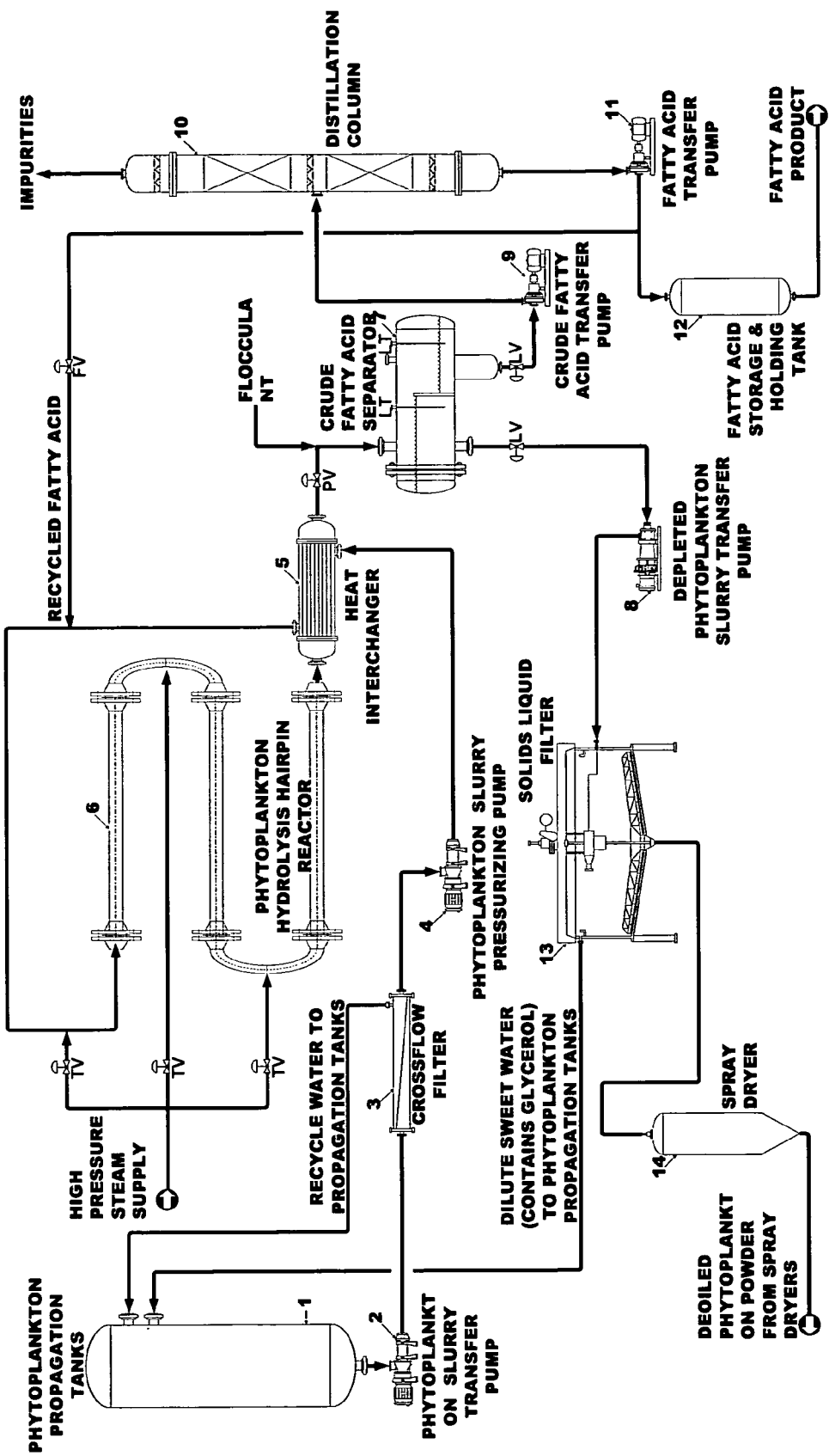
FIG. 2 is a schematic diagram of a system including a horizontal hairpin reactor for carrying out the process of this invention.

A block schematic of one version of the process that we have invented is presented in FIG. 2.

The continuous process begins with the phytoplankton being suctioned out of the propagation tanks 1 in the form of a slurry ("soup") into the system. A low pressure slurry transfer pump 2 is used for this purpose. The weight content of the biomass in the slurry can range from less than 1 wt % up to 15 wt %.

Depending upon the physical and chemical properties of the particular phytoplankton, the slurry may be concentrated by using a crossflow filtration system 3 equipped with inorganic membranes, ceramic membranes or hollow fiber membranes. The weight content of the biomass in the slurry leaving the concentrator can range from more than 5 wt % up to 20 wt %.

The phytoplankton slurry that is either directly drawn out of the propagation tanks 1, or having gone through the concentrator 3, is pressurized to a level ranging from 20 bar up to 200 bar by, means of a slurry pressurizing pump 4. The exact pressure will depend upon the physical and chemical properties of the particular phytoplankton that is being processed, and the weight percentage content of the biomass in the slurry.

The heart of the system consists of a hydrolysis reactor 6 that is described in greater detail below. This reactor serves to convert the immobilized lipids contained in the phytoplankton into fatty acids. Depending upon the physical and chemical properties of the phytoplankton that is being processed, and the weight percentage content of the biomass in the slurry, the temperature inside this reactor will range from 200° C. up to 700° C.

The phytoplankton slurry leaving the pressurizing pump 4 is sent through a high efficiency heat interchanger 5 prior to entry into the hydrolysis reactor 6. The purpose of this heat interchanger 5 is to transfer as much heat as possible from the higher temperature processed slurry stream leaving the reactor to the ambient temperature incoming slurry stream entering the reactor. In order to minimize heat loss, the heat interchanger is heavily insulated on the outside.

A certain amount of fatty acid product from the tail end of the process is recycled through the fatty acid transfer pump 8 and added into the preheated incoming phytoplankton slurry before it enters the hydrolysis reactor 6. This recycled fatty acid product serves as a catalyst for promoting the hydrolysis reaction. Provision is also made for injecting controlled amounts of high pressure steam into the hydrolysis section at one or more points. As an example, FIG. 2 shows three points at which high pressure steam is injected into the hydrolysis section.

The hydrolysis reactor 6 features a tubular configuration that is designed for operation in the co-current flow mode. In other words, the preheated incoming slurry, the recycled fatty acid product and the injected steam all move in the same direction. The volume of steam injected at each point is controlled by a temperature control loop and valve. The amount of recycled fatty acid product that is added into the incoming slurry is controlled by a flow control loop and valve (not shown).

The length and diameter of the reactor 6 will depend upon the desired residence time within the reactor 6, which in turn will depend upon the physical and chemical properties of the particular phytoplankton that is being processed, and the weight percentage content of the biomass in the slurry. In order to minimize heat loss, the entire hydrolysis reactor 6 section is heavily insulated.

Figure 3:
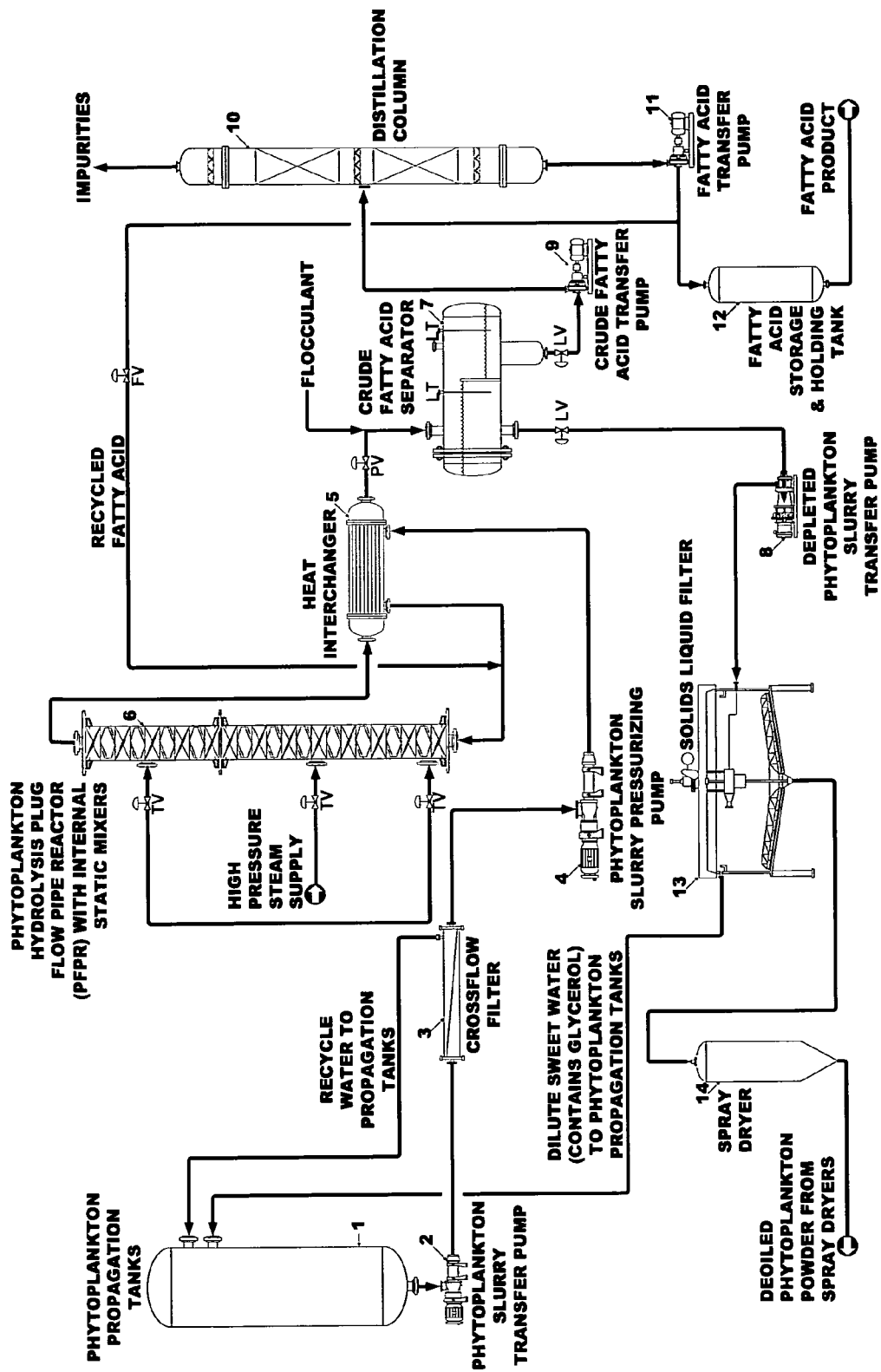
FIG. 3 is a schematic diagram of a system including a vertical pipe reactor for carrying out the process of this invention.
Figure 4:
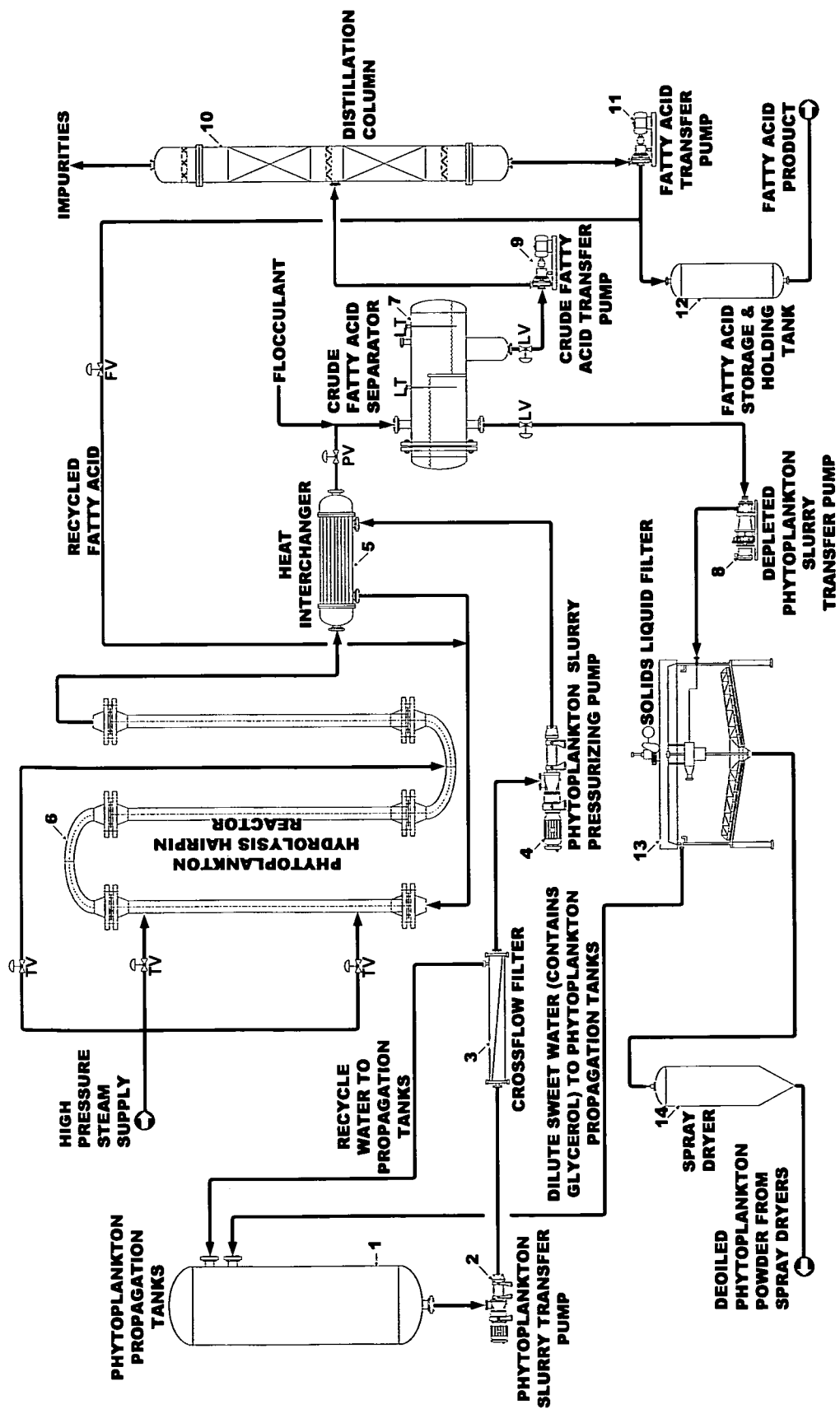
FIG. 4 is a schematic diagram of a system including a vertical hairpin reactor for carrying out the process of this invention.

The hydrolysis reactor 6 shown in FIG. 2 is a horizontal hairpin reactor. In another embodiment, as shown in FIG. 3, the hydrolysis reactor 6 is a straight vertical pipe reactor with internal static mixers, or as shown in FIG. 4, the hydrolysis reactor 6 is a vertical hairpin arrangement. The hairpin reactors (horizontal and vertical) may or may not be equipped with internal static mixers.

Figure 5:
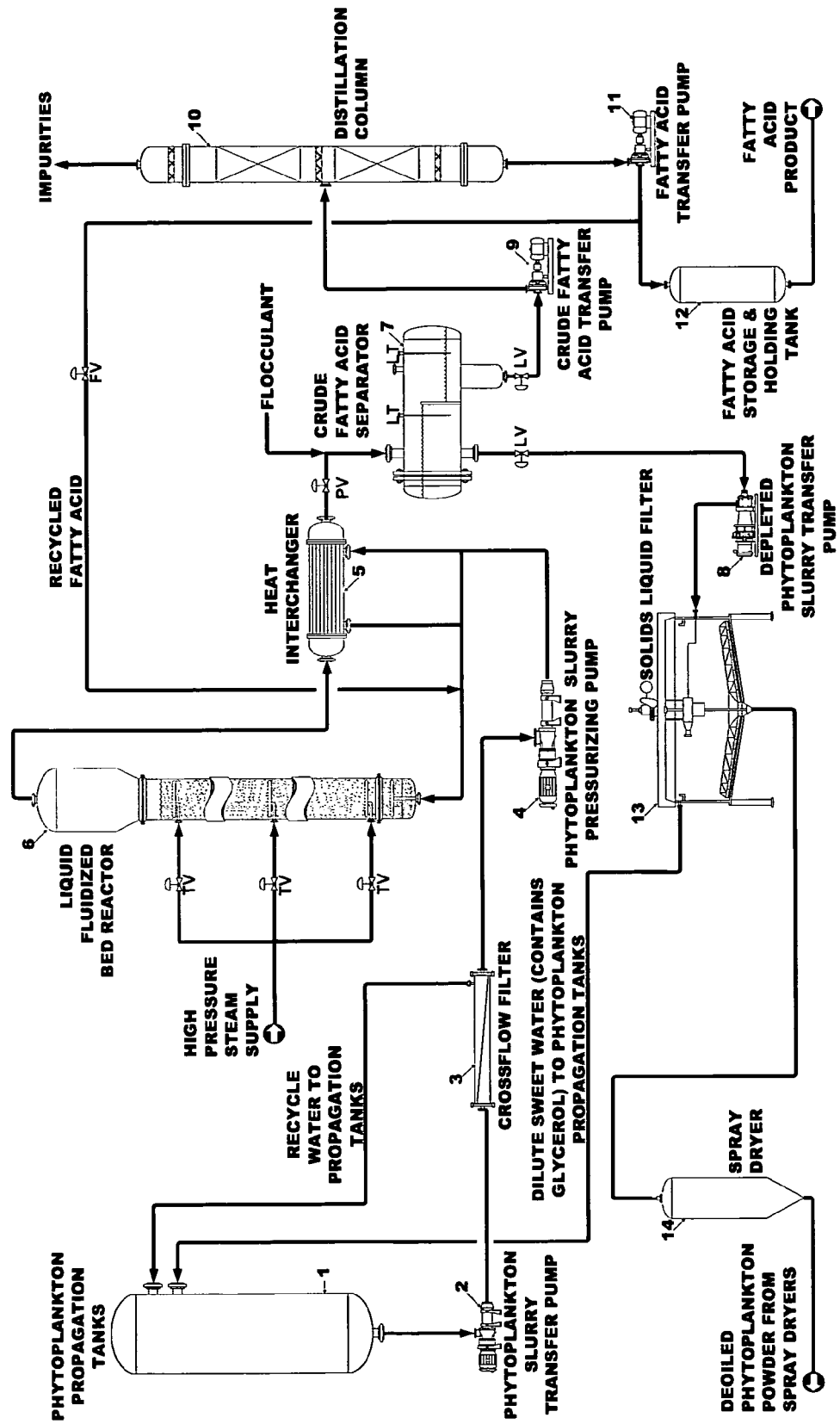
FIG. 5 is a schematic diagram of a system including a cylindrical fluidized bed reactor for carrying out the process of this invention.
Figure 6:
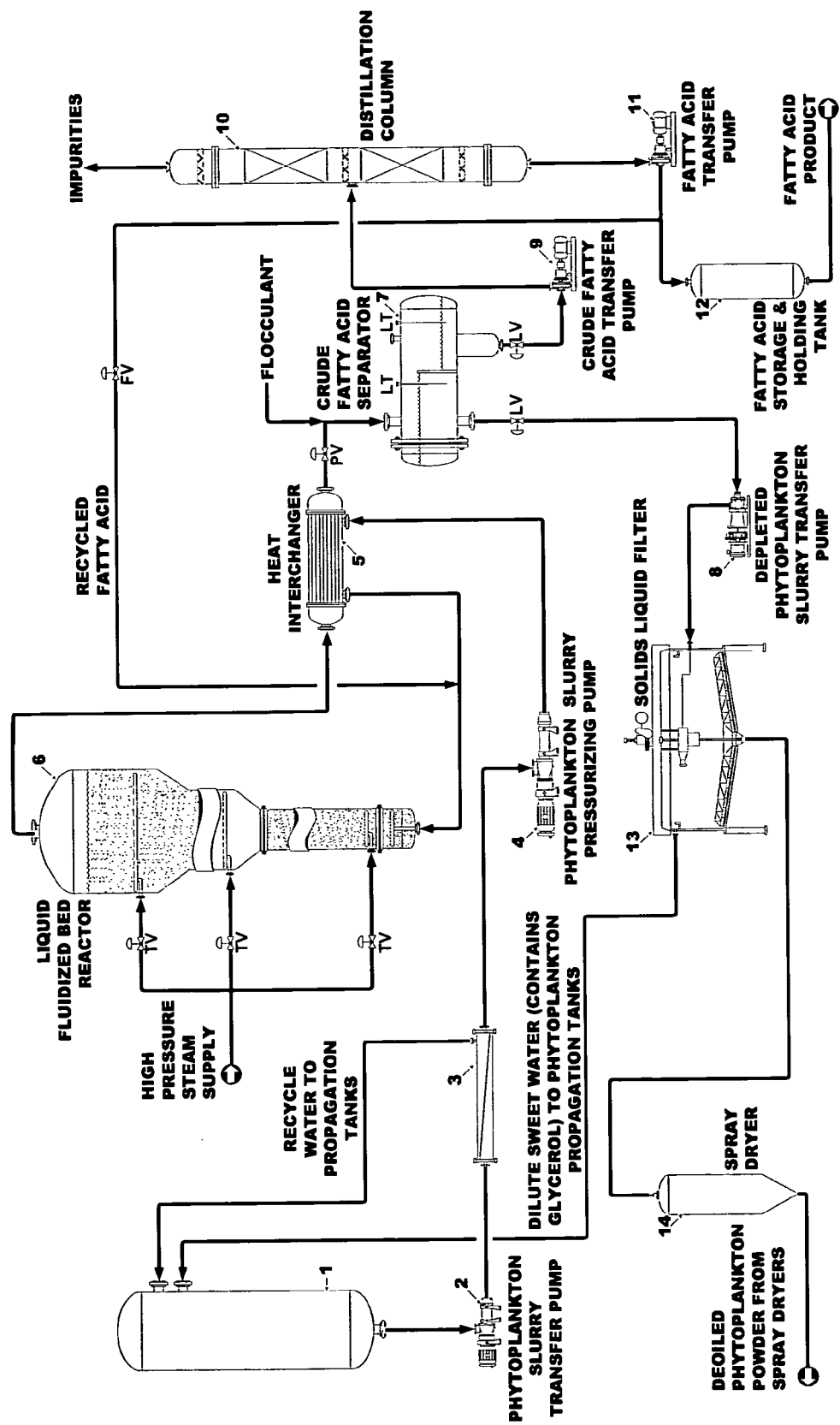
FIG. 6 is a schematic diagram of a system including a multi-stage progressively expanding fluidized bed reactor for carrying out the process of this invention.

In a fourth and fifth embodiment, the hydrolysis reactor 6 is a cylindrical fluidized bed reactor as shown in FIG. 5, or a multi-stage progressively expanding fluidized bed reactor as shown in FIG. 6. The process inputs to both these fluidized reactor variants will be 1) the preheated phytoplankton slurry, 2) controlled amount of high pressure steam, and 3) recycled fatty acid product as a catalyst. Both these fluidized bed reactor variants are designed to operate as backmix reactors with the inclusion of an inert solid particulate fluidizing media, or a base/alkaline heterogeneous catalyst as the fluidizing media. The overall dimensions and geometry of these two fluidized bed reactor variants will depend upon the desired residence time within the reactor, which in turn will depend upon the physical and chemical properties of the particular phytoplankton that is being processed, and the weight percentage content of the biomass in the slurry.

The hot effluent slurry leaving the hydrolysis reactor 6 goes through the heat interchanger 5 where its heat is transferred to the incoming ambient temperature slurry. After giving up its heat, this effluent slurry is depressurized into a horizontal crude fatty acid separator 7. The crude fatty acid product that will float on top will continuously overflow over a weir into the product side of the separator 7.

The elemental composition (wt %) of the crude fatty acid product is displayed in Table 2.

TABLE 2

ELEMENTAL COMPOSITION (WT %) OF CRUDE FATTY ACID PRODUCT

| Component | | | | |
|---|---|---|---|---|
| C | H | O | N | S |
| Wt % 74.14 | 9.69 | 11.90 | 3.47 | 0.80 |

This crude fatty acid product has the approximate formula of:

$C_{24.9}H_{38.8}O_3NS_{0.1}$. Its major impurity is the nitrogen compound which can be represented by Indole, $C_8H_7N$. The trace amount of sulfur content just forms hydrogen sulfide in the hydrolysis reactor and leaves the system. The composition of crude fatty acid obtained from phytoplankton by this invention is shown in Table 3.

TABLE 3

COMPOSITION OF CRUDE FATTY ACID OBTAINED FROM PHYTOPLANKTON BY THIS INVENTION

| Structure | Name | Wt% |
|---|---|---|
| $C_{16.9}H_{31.6}O_3$ | Crude Fatty Acid | 70.11 |
| $C_8N_7N$ | Indole | 29.04 |
| $H_2S$ | Hydrogen Sulfide | 0.85 |

$32C_{24.9}H_{38.8}O_3NS_{0.1} \longrightarrow 32C_{16.9}H_{31.6}O_3 + 32C_8H_7N + 3.2\,H_2S$ $32C_{16.9}H_{31.6}O_3 \xrightarrow{+H_2} 13C_{16}H_{30}O_2 + 10C_{16}H_{32}O_2 + 3C_{18}H_{34}O_2 + C_{18}H_{36}O_2 + 2C_{14}H_{28}O_2 + C_{20}H_{40}O_2 + 10.3\,C_3H_8O_3 + \text{Others}$ Flocculant may or may not be selectively added into the crude fatty acid separator 7. Depending upon the action required and environmental considerations, the flocculant is either a chemical compound, or a natural biodegradable polymeric substance such as polyaspartic acid, chitosan or sodium alginate.

The crude fatty acid product is continuously drawn out of the separator 7 using a level control loop slaved to a level transmitter and a level control valve (not shown). The crude fatty acid product is pumped by the crude fatty acid transfer pump 9 into a single distillation column 10 to get purified. The purified fatty acid product is obtained at the bottom of the distillation column 10. A fatty acid transfer pump 11 is used to send most of this product to a final storage and holding tank 12. A predetermined fraction of this fatty acid product is recycled as a catalyst into the hydrolysis slurry feed stream under the auspices of a flow control loop that includes a flow control valve (not shown).

The depleted slurry from the separator 7 containing the deoiled phytoplankton biomass and water containing glycerol and other water solubles is also drawn out of the separator 7 under the auspices of its own flow control loop that includes a flow control valve (not shown). This depleted slurry is continuously pumped by the depleted phytoplankton slurry transfer pump 8 into a solids-liquid filter 13 that affects the following separations:
  1. A dilute "sweet water" stream consisting of water, glycerol and other water solubles is pumped back into the phytoplankton propagation tanks 1.
  2. The concentrated deoiled wet biomass is sent into a spray dryer 14, after which this product is bagged and shipped for use as animal food ingredient.

Nutrient Stream is Recycled to Promote Phytoplankton Cultivation

A significant body of research has shown that the addition of glycerol serves to enhance the growth of phytoplankton. The two papers that best summarize this subject are:
  1. *"Utilization of glycerol as carbon source on the growth, pigment and lipid production in spirulina platensis,"* by M. S. Narayan, G. P. Manoj, K. Vatchravelu, N. Bhagyalakshmi and M. Mahadevaswamy, *International Journal of Food Sciences and Nutrition*, November. 2005; 56(7): 521-528.
  2. *"Producing Docosahexaenoic Acid (DHA)-Rich Algae from Biodiesel-Derived Crude Glycerol: Effects of Impurities on DHA Production and Algal Biomass Composition,"* by Denver J. Pyle, Rafael A. Garcia and Zhiyou Wen, *Journal of Agricultural and Food Chemistry*, May 2008, 56: 3933-3939.

EXAMPLE

A 600,158 lb/hr of slurry ("soup") containing 5 wt % of phytoplankton are suctioned out of the propagation tanks and is transferred into the system via a low pressure slurry transfer pump. This slurry is concentrated by using a crossflow filtration unit equipped with inorganic membranes. The weight content of the phytoplankton in the slurry leaving the concentrator is 15 wt % with a flow rate of 200,053 lb/hr.

The concentrated phytoplankton slurry is pressurized to 1015 psia (70 bar) by means of a slurry pressurizing pump. The slurry leaving the pressurizing pump is sent through a high efficiency heat interchanger prior to entry into the hydrolysis reactor. The heat interchanger can heat up the slurry from ambient temperature to 500° F. (260° C.).

6670 lb/hr of high pressure steam at 1050 psia (72 bar) are injected into the hydrolysis reactor at three injection points to keep the reactor temperature at 518° F. (270° C.). A small amount of hydrogen (120 lb/hr) is also injected along with the high pressure steam in order to support the hydrogenation reactions in the reactor. 900 lb/hr of fatty acid product from the tail end of the process are recycled through the fatty acid transfer pump and added into the preheated phytoplankton slurry before it enters the hydrolysis reactor. This recycled fatty acid product serves as a catalyst for promoting the hydrolysis reactions.

The immobilized lipids contained in the phytoplankton is converted into crude fatty acid in the hydrolysis reactor. At 518° F. (270° C.) it takes about 30 minutes to get a good yield of crude fatty acid product. The hot effluent slurry leaving the hydrolysis reactor goes through the heat interchanger where its heat is transferred to the incoming ambient temperature slurry. After giving up its heat, this effluent slurry is depressurized into a horizontal crude fatty acid separator. The crude fatty acid product that floats on top is continuously overflowed over a weir into the product side of the separator. The glycerol produced (949 lb/hr) during the hydrolysis reactions will stay along with the carbohydrates and protein in the water phase since they are all water soluble.

TABLE 4

COMPOSITION OF CRUDE FATTY ACID OBTAINED FROM PHYTOPLANKTON BY THIS INVENTION

| Structure | Name | Flow Rate, lb/hr |
|---|---|---|
| $C_{16}H_{30}O_2$ | Palmitoleic Acid | 3674 |
| $C_{16}H_{32}O_2$ | Palmitic Acid | 2849 |

TABLE 4-continued

COMPOSITION OF CRUDE FATTY ACID OBTAINED FROM
PHYTOPLANKTON BY THIS INVENTION

| Structure | Name | Flow Rate, lb/hr |
|---|---|---|
| $C_{18}H_{34}O_2$ | Oleic Acid | 941 |
| $C_{18}H_{36}O_2$ | Stearic Acid | 316 |
| $C_{20}H_{40}O_2$ | Arachidic Acid | 347 |
| $C_{14}H_{28}O_2$ | Myristic Acid | 507 |
| $C_3H_8O_3$ | Glycerol | Trace |
| $C_8H_7N$ | Indole | 3749 |
| $H_2O$ | Water | Trace |
| Others | Others | 378 |
| Total | | 12,762 |

The impurity (Indole) content in the crude fatty acid product can be separated by a single distillation column. Indole with a purity of 99.62 wt % is recovered at the overhead of the column and the purified fatty acid product is obtained at the bottom of the distillation column.

TABLE 5

PURIFIED FATTY ACID PRODUCT

| Structure | Name | Flow Rate, lb/hr | Wt % |
|---|---|---|---|
| $C_{16}H_{30}O_2$ | Palmitoleic Acid | 3660 | 40.67 |
| $C_{16}H_{32}O_2$ | Palmitic Acid | 2849 | 31.66 |
| $C_{18}H_{34}O_2$ | Oleic Acid | 941 | 10.46 |
| $C_{18}H_{36}O_2$ | Stearic Acid | 316 | 3.51 |
| $C_{20}H_{40}O_2$ | Arachidic Acid | 347 | 3.86 |
| $C_{14}H_{28}O_2$ | Myristic Acid | 507 | 5.64 |
| $C_8H_7N$ | Indole | 8 PPMW | 0.9 PPBW |
| Others | Others | 378 | 4.20 |
| Total | | 8999 | 100.00 |

900 lb/hr of the purified fatty acid product serving as a catalyst for promoting the hydrolysis reaction are recycled back to the reactor, which gives a net fatty acid product of 8099 lb/hr.

The depleted slurry (194,811 lb/hr) from the separator containing the deoiled phytoplankton, water, glycerol and other water soluble is drawn out of the separator and pumped into the solid-liquid filter. The liquid stream (109,073 lb/hr) from the solid-liquid filter consisting of water, glycerol and other water soluble is pumped back into the phytoplankton propagation tanks. The wet solid stream which contains 17,148 lb/hr solids, 366 lb/hr glycerol, 68,224 lb/hr water and other water soluble is sent into a spray dryer. The spray dryer can dry the wet solid from 80 wt % moisture level down to 20 wt %, after which this product is bagged and shipped for use as animal food ingredient.

TABLE 6

ANIMAL FOOD INGREDIENT

| Composition | Flow Rate, lb/hr | Wt % |
|---|---|---|
| Protein & Carbohydrates | 17,148 | 78.66 |
| Glycerol | 366 | 1.68 |
| Water | 4,287 | 19.66 |
| TOTAL | 21,801 | 100.00 |

In addition to making fatty acids directly from phytoplankton, our process also serves to promote and accelerate the cultivation of phytoplankton in the propagation tanks. The dilute "sweet water" stream containing water, glycerol and other solubles leaving the solids-liquid filter is continuously pumped back into the phytoplankton propagation tanks. The carbon in the glycerol is saved and utilized as a nutrient to enhance the growth of phytoplankton.

What is claimed is:

1. A continuous process for the production of fatty acids from phytoplankton, said process comprising:
   a) Pressurizing a concentrated slurry with the weight content of the biomass from 5 wt % to 20 wt % to a pressure between 20 and 200 bar;
   b) performing thermal hydrolysis on the slurry stream using steam as the heat source to convert the immobilized lipids into free fatty acids of varying lengths at temperatures ranging from 200 to 700° C.;
   c) recovering the heat of the system by interchanging the hydrolysis product with the incoming slurry stream;
   d) depressurizing the hydrolysis product stream in a separator to release the cooled fatty acids from the depleted slurry;
   e) feeding the cooled fatty acids stream to a distillation tower for purification;
   f) feeding the depleted slurry comprisinq the deoiled phytoplankton biomass and water containing glycerol and other water solubles into the solids-liquid filter;
   g) separating the leftover biomass from the glycerin and water stream by means of filtration; and
   h) spray-dryinq the biomass for use as a food ingredient for animal feed.

2. The process as set forth in claim 1, wherein the weight content of the biomass in the slurry ranges from less than 1 wt % up to 15 wt %.

3. The process according to claim 1, wherein the biomass slurry is concentrated to between 5 wt % and 20 wt % by means of a crossflow filtration system and recycling the water.

4. The process according to claim 1, wherein the temperature depends upon the physical and chemical properties of the phytoplankton that is being processed, and the weight percentage content of the biomass in the slurry.

5. The process according to claim 1, wherein hydrogen equivalent to 1.5 wt % of the fatty acid content in the phytoplankton is injected along with the high pressure steam in order to support the hydrogenation reactions.

6. The process as set forth in claim 1, wherein a tubular configuration is designed for operation in the cocurrent flow mode, the preheated incoming slurry, the recycled fatty acid product and the injected steam all move in the same direction.

7. The process according to claim 1, wherein the slurry consisting of phytoplankton in water does not need to be significantly dewatered and/or dried.

8. The process as set forth in claim 1, wherein there is no need to extract the immobilized lipids in order to make fatty acids.

9. The process as set forth in claim 1 that includes a horizontal hairpin hydrolysis reactor with or without internal static mixers.

10. The process as set forth in claim 1 that includes a vertical pipe hydrolysis reactor with internal static mixers.

11. The process as set forth in claim 1 that includes a vertical hairpin hydrolysis reactor with or without internal static mixers.

12. The process as set forth in claim 1 that includes a multi-stage progressively expanding fluidized bed hydrolysis reactor.

13. The process according to claim 1, wherein about 10 wt % of the fatty acid product from the tail end of the process is added to the preheated slurry stream to promote the reaction.

14. The process according to claim 1 that includes the addition of a solid particulate fluidizing media to enable operation in a backmix mode, wherein the fluidizing media is an inert substance or a base/alkaline heterogeneous catalyst that serves to accelerate the reaction.

15. The process wherein a flocculant is or is not selectively added into the crude fatty acid separator, depending upon the action required and environmental considerations, and the flocculant is either a chemical compound, or a natural biodegradable polymeric substance selected from a group consisting of polyaspartic acid, chitosan or sodium alginate.

16. The process as set forth in claim 1, wherein the depleted slurry from the separator containing the deoiled phytoplankton biomass and water containing glycerol and other waste solubles is also drawn out of the separator and the depleted slurry is continuously pumped into a solids-liquid filter that affects the following separations:
   a) A dilute stream consisting of water, glycerol and other water solubles is pumped back;
   b) The concentrated deoiled wet biomass is sent into a spray dryer, after which this product is bagged and shipped for use as animal food ingredient.

17. The process as set forth in claim 1, wherein the major impurity content in the crude fatty acid product, $C_{24.9}H_{38.8}O_3NS_{0.1}$ is the nitrogen compound which is represented by indole, $C_8H_7N$ which with a purity of about 99.62 wt % is recovered at the overhead of the distillation column.

18. The process as set forth in claim 1, wherein the trace amount of sulfur content in the crude fatty acid product, $C_{24.9}H_{38.8}O_3NS_{0.1}$ just forms hydrogen sulfide in the hydrolysis reactor and leaves the system.

* * * * *